United States Patent
Shetty

(10) Patent No.: US 11,304,983 B2
(45) Date of Patent: Apr. 19, 2022

(54) MEDICATED HONEY AND METHOD OF PREPARATION THEREOF

(71) Applicant: Muniyal Ayurvedic Research Centre, Manipal (IN)

(72) Inventor: M Vijayabhanu Shetty, Karnataka (IN)

(73) Assignee: Muniyal Ayurvedic Research Centre, Manipal (IN)

( * ) Notice: Subject to any disclaimer, the term of this patent is extended or adjusted under 35 U.S.C. 154(b) by 615 days.

(21) Appl. No.: 16/142,260

(22) Filed: Sep. 26, 2018

(65) Prior Publication Data

US 2019/0022150 A1  Jan. 24, 2019

Related U.S. Application Data

(60) Provisional application No. 62/563,910, filed on Sep. 27, 2017.

(51) Int. Cl.

| | |
|---|---|
| *A61K 35/644* | (2015.01) |
| *A61P 35/00* | (2006.01) |
| *A61P 39/06* | (2006.01) |
| *A61K 45/06* | (2006.01) |
| *A23L 33/10* | (2016.01) |
| *A23L 21/25* | (2016.01) |
| *A23K 50/90* | (2016.01) |

(52) U.S. Cl.
CPC ............ *A61K 35/644* (2013.01); *A23K 50/90* (2016.05); *A23L 21/25* (2016.08); *A23L 33/10* (2016.08); *A61K 45/06* (2013.01); *A61P 35/00* (2018.01); *A61P 39/06* (2018.01)

(58) Field of Classification Search
CPC .... A61K 2300/00; A61K 36/59; A61K 33/10; A61K 33/26; A61K 33/30; A61K 33/34; A61K 36/53; A61K 36/67; A61K 36/68; A61K 36/81; A61K 36/8965; A61K 36/9066; A61K 36/9068; A61K 36/232; A61K 36/28; A61K 36/39; A61K 36/484; A61K 36/882; A61K 45/06; A61K 35/644; A61K 33/24; A61K 47/02; A61K 47/46; A61K 9/0053; A61K 9/006; A61K 9/0095; A61K 9/1075; A23L 21/25; A23L 33/10; A23L 33/105; A23L 33/16; A23L 5/00; A61P 35/02; A61P 35/00; A61P 37/04; A61P 39/06; A23K 50/90; A23V 2002/00

See application file for complete search history.

(56) References Cited

U.S. PATENT DOCUMENTS

2019/0022150 A1* 1/2019 Shetty .................. A61K 35/644

OTHER PUBLICATIONS

Wannarka, Megan "Nectar, Pollen, and Propolis Source Plants" Honey Bee Plants in Grenada, Eastern Caribbean, 2016, 160pp. (Year: 2016).*
Islam, MR; Pervin, T; Hossain, H; Saha, B; Hossain, SJ "Physicochemical and Antioxidant Properties of Honeys from the Sundarbans Mangrove Forest of Bangladesh" Preventive Nutrition and Food Science, Dec. 31, 2017,22(4),pp. 335-344; DOI: 10.3746/pnf.2017.22.4.335. (Year: 2017).*
The Government of India, Biological Diversity Act, 2002.†

* cited by examiner
† cited by third party

*Primary Examiner* — Aaron J Kosar
(74) *Attorney, Agent, or Firm* — Pilloff Passino & Cosenza LLP; Sean A. Passino; Rachel K. Pilloff

(57) ABSTRACT

Medicated honey and method of preparing the same are disclosed herein. The disclosed honey is obtained by feeding honeybees with bee-feed obtained from medicinal plants. The medicated honey disclosed herein is such that it has anti-oxidant and anti-cancer properties. The embodiments disclosed herein may be instrumental in strengthening the immune system, as an anti-cancer agent and as an anti-oxidant.

10 Claims, 3 Drawing Sheets

MEDICATED HONEY AND METHOD OF PREPARATION THEREOF

CROSS REFERENCE TO RELATED APPLICATION

This application is based on and claims the benefit of U.S. Provisional Application 62/563,910 filed on the 27 of Sep. 2017, the contents of which are incorporated herein by reference in their entirety.

TECHNICAL FIELD

The embodiments disclosed in this specification relates to medicated honey, and more particularly to its anti-cancer and anti-oxidant properties. It also relates to the process for the preparation of medicated honey.

BACKGROUND

Honey, a syrupy sweet liquid naturally produced by Honey bees has always had a special place since ancient times. Honey bees collect nectar from various flowers which is then converted to honey by enzymatic activity and regurgitation.

Raw honey is usually murky and comprises of increased levels of bee pollen, amino acids, sugars, antimicrobial agents and anti-oxidants. Honey that is commercially available is processed and is clear in appearance. Processing of honey is usually performed by heating and straining under specific conditions before packaging to ensure it is devoid of local contamination and debris. However, many nutrients that are heat sensitive disintegrate during this process and hence may be lost during processing making the product less nutritive.

Honey in any form is known to possess therapeutic properties. Since ancient times, honey has been used to treat wounds, ulcers, skin conditions, etc. It is also used to improve digestion, relieve nausea, lower cholesterol, reduce inflammation, relieve sore throat and enhance taste among other uses. In Ayurveda, honey is considered as a medicine and a medium for administering medicine. It is used in formulations containing herbs, minerals, etc. to treat stomach, skin, eyes, heart, lungs, mouth, and so on.

Numerous varieties of honey are known. Honey varies in flavor and appearance depending on the source of the nectar. Some of the commonly known types include Buckwheat honey, Neem honey, Basswood honey, Acacia honey, Manuka honey and so on. The flower source used by honeybees to produce honey is known to influence the quality of honey. The therapeutic attributes of the source are often reflected in the attributes of the honey obtained.

Various attempts have been made to obtain honey having specific therapeutic properties by creating an ecosystem for the cultured bees to feed on selected flowers. Given the increasing burden of diseases including cancer and other lifestyle diseases on the society, there is a growing need for identifying and obtaining rich sources of antioxidants. Several fruits, medicinal plants and herbs are known for its antioxidative and anti-cancerous properties. There is however a need for preparation of honey which is not only nutritive but also rich in antioxidant.

OBJECTS OF THE DISCLOSED EMBODIMENTS

The principal object of the embodiments disclosed herein is to provide a method of producing medicated honey.

Another object of the invention is to provide honey having medicinal properties, such as anti-oxidant and anti-cancer properties.

Yet another object of the invention is to provide a method for the management/prevention of cancer.

These and other objects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF FIGURES

The embodiments disclosed herein are illustrated in the accompanying drawings, throughout which like reference letters indicate corresponding parts in the various figures. The embodiments herein will be better understood from the following description with reference to the drawings, in which.

DETAILED DESCRIPTION

Figure 1:
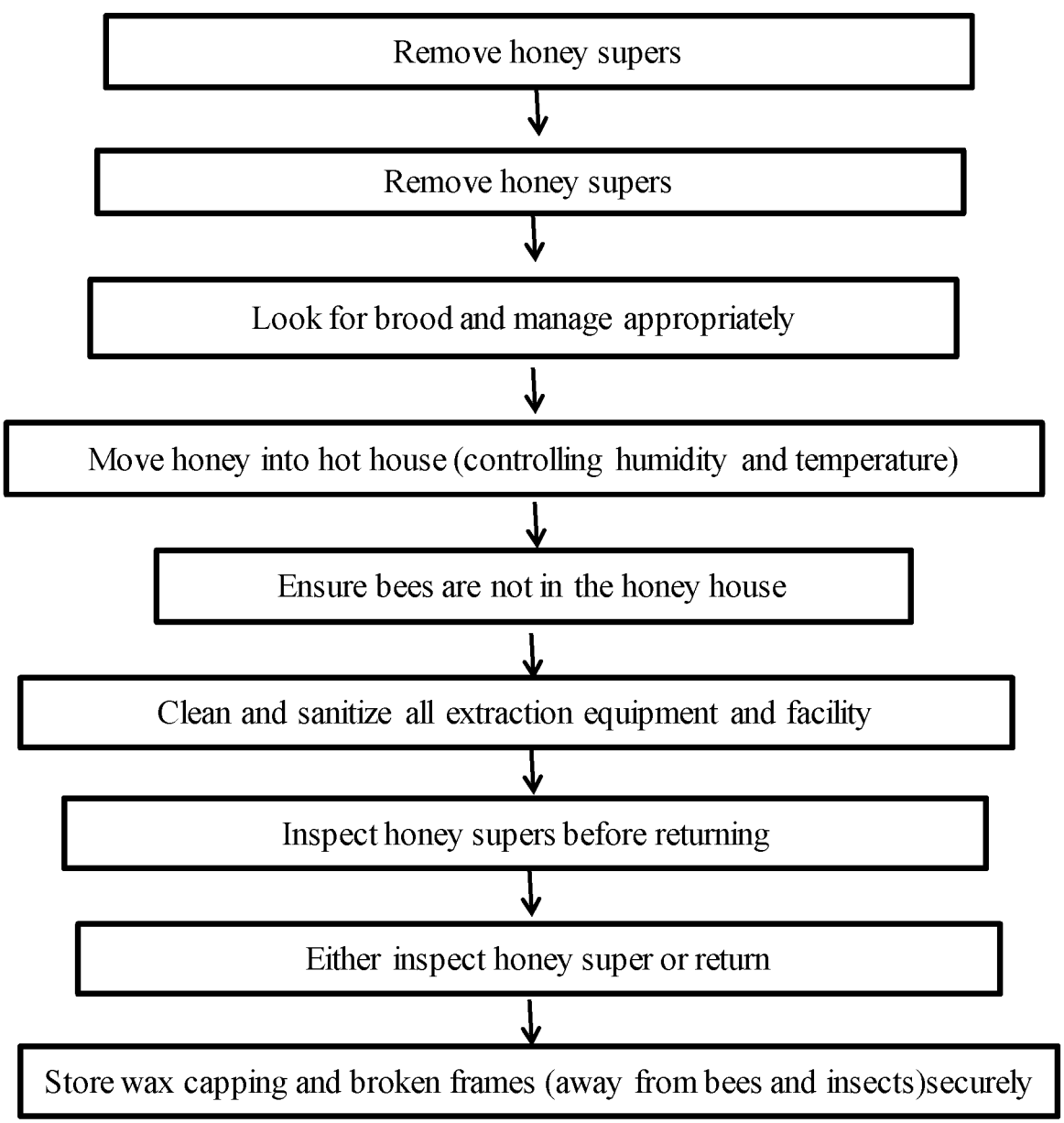
FIG. 1 depicts a flowchart for method of honey extraction.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments disclosed here may be practiced and to further enable those of skill in the art to practice these embodiments. Accordingly, the examples should not be construed as limiting the scope of the embodiments herein.

The embodiments herein achieve honey having medicinal properties, and a process for its preparation. The honey disclosed in the various embodiments herein is medicated honey having anti-oxidant and anti-cancer properties. Medicinal properties may further include antimicrobial, antiulcer, cytoprotective, chemoprotective, wound healing, anti-acne, hepatoprotective, antiviral, filaricidal, anti-allergy, anti-diabetic, analgesic, antipyreticproperties and so on.

The embodiments herein also achieve a medicated honey instrumental as an anti-oxidating and anti-cancer agent. In various embodiments, the medicated honey may also be used to prepare medicament having anti-oxidative and anti-cancer properties.

Further embodiments disclose a method for the management or prevention of cancer. Also disclosed herein are methods of improving general health.

The disclosed embodiments further include a method of producing medicated honey. In an embodiment, the method includes feeding honeybees with bee-feed obtained from various medicinal plants. The medicinal plants may be any plant including herbs, shrubs, trees, vines, etc that is known to have medicinal properties.

Medicated Honey

Disclosed herein are embodiments of medicated honey of therapeutic value. In an embodiment, the medicated honey is one having anti-oxidant properties. In another embodiment, the medicated honey is such that it includes anti-cancer properties.

In an embodiment, the medicated honey is one that is obtained by feeding honeybees with bee-feed obtained from at least one of *Plumeria rubra, Vinca rosea, Ageretum conzyoides, Calotropis gigantea, Calotropis procera, Nerium indicum, Thevetia neriifolia, Jasminum officinale, Jasminum auriculatum, Musa paradisiaca, Jasminum humile, Nyctanthes abor-tristis, Ocimum sanctum, Ocimum gratissimum, Tabernaemontana divaricata, Tridax procumbens, Cassia auriculata, Hibiscus vitifolius, Sesbania grandiflora, Nymphaea alba, Saraca asoca, Hibiscus alba, Couroupita guianensis* and *Plumbago rosea*. In an embodiment, the bee-feed may include nectar of the medicinal plants. In another embodiment, the bee-feed may include an extract obtained from the medicinal plants.

In an embodiment, the honey obtained may be combined with other ingredients such as minerals, vitamins, amino acids, herbal extracts, therapeutic agents, etc. The therapeutic agents that may be used include anti-oxidants, anticancer, antimicrobial, antiulcer, cytoprotective, chemoprotective, wound healing, anti-acne, hepatoprotective, antiviral, filaricidal, anti-allergy, anti-diabetic, analgesic, antipyretic agents and so on. In an embodiment, the medicated honey obtained may further be used to prepare medicament of therapeutic value.

Table. 1 is a table illustrating the characteristics of an embodiment of medicated honey disclosed herein.

Disclosed herein are embodiments of a method for producing medicated honey. In an embodiment, the method includes providing honeybees with bee-feed obtained from medicinal plants having anti-cancer and anti-oxidant properties; extracting the honey produced by the honeybees; and processing the extracted honey.

The bee-feed used may include plant nectar and/or herb extract/decoction of medicinal plants. In an embodiment, the bee-feed is plant nectar of atleast one of *Plumeria rubra, Vinca rosea, Ageretum conzyoides, Calotropis gigantea, Calotropis procera, Nerium indicum, Thevetia neriifolia, Jasminum officinale, Jasminum auriculatum, Musa paradisiaca, Jasminum humile, Nyctanthes abor-tristis, Ocimum sanctum, Ocimum gratissimum, Tabernaemontana divaricata, Tridax procumbens, Cassia auriculata, Hibiscus vitifolius, Sesbania grandiflora, Nymphaea alba, Saraca asoca, Hibiscus alba, Couroupita guianensis* and *Plumbago rosea*. The bee-feed may alternatively or additionally include a herb extract obtained from atleast one of *Plumeria rubra, Vinca rosea, Ageretum conzyoides, Calotropis gigantea, Calotropis procera, Nerium indicum, Thevetia neriifolia, Jasminum officinale, Jasminum auriculatum, Musa paradisiaca, Jasminum humile, Nyctanthes abor-tristis, Ocimum sanctum, Ocimum gratissimum, Tabernaemontana divaricata, Tridax procumbens, Cassia auriculata, Hibiscus vitifolius, Sesbania grandiflora, Nymphaea alba, Saraca asoca, Hibiscus alba, Couroupita guianensis* and *Plumbago rosea*. In an embodiment, the herb extract may be obtained by techniques generally known in the art such as grinding, extraction, boiling, centrifugation, etc, of one or more medicinal plants.

In an embodiment, the method includes maintaining a controlled system. The controlled system may be conditions that are generally considered suitable for honeybees to produce honey. In an embodiment, the controlled system

TABLE 1

| Physical constants | API standards | Values in the sample |
| --- | --- | --- |
| Nature | Viscous, translucent liquid. | Viscous, translucent liquid. |
| Color | Yellowish to dark brown | Yellowish to dark brown |
| Odor | Agreeable | Agreeable |
| Taste | Sweet | Sweet |
| Solubility | Initially settles as a lump at the bottom, on mixing well dissolves in water and alcohol. | Initially settles as a lump at the bottom, on mixing well dissolves in water and alcohol. |
| Invert Sugars | 70-80% | 72.50% |
| Sucrose | 0.1-10% | 0.12% |
| Flame test | Burns | Burns |
| Absorption test | Totally absorbed into blotting paper | Totally absorbed into blotting paper |
| Test for reducing sugars | Positive | Positive |
| Selivanoff's test | Rose color indicating glucose | Positive |
| Test for dextrin | Negative | Negative |
| Fiehe's test | Transient red color | Positive |
| Anilin chloride test | Absence of red/crimson color | No crimson/red colour appeared |

In an embodiment, the honey is such that it is translucent, yellowish dark brown, viscous liquid, having 72.5% invert sugars and 0.12% sucrose. In an embodiment, the honey tested positive for reducing sugars, Selivanoff's test and Fiehe's test, and negative for Aniline chloride test and Test for dextrin.

The honeybees employed to obtain the medicated honey disclosed in the various embodiments herein may be of any species known in the art. In an embodiment, the honeybees used may be of the species *Apisindica* or *Apiscerena*.

Method includes maintaining a condition wherein the temperature is in the range of 32° C. and 36° C. and relative humidity is in the range of 60% to 75%. The bee-feed may be provided for a preferable period of about 100 to 150 days. It would be apparent to a person skilled in the art that many modifications in the method may be practiced without departing from the scope of the present invention.

The honey produced by the bees upon providing the bee-feed, according to the various embodiments herein, may be extracted by method generally known in the field. In an embodiment, extraction may be performed by removing honey super, looking for brood and managing appropriately, moving honey into hot houses and extracting honey using an extractor. The honey supers, after extraction may further be stored or returned to the hive. In an embodiment extraction of honey may be performed by generally known commercial extractors.

Figure 2:
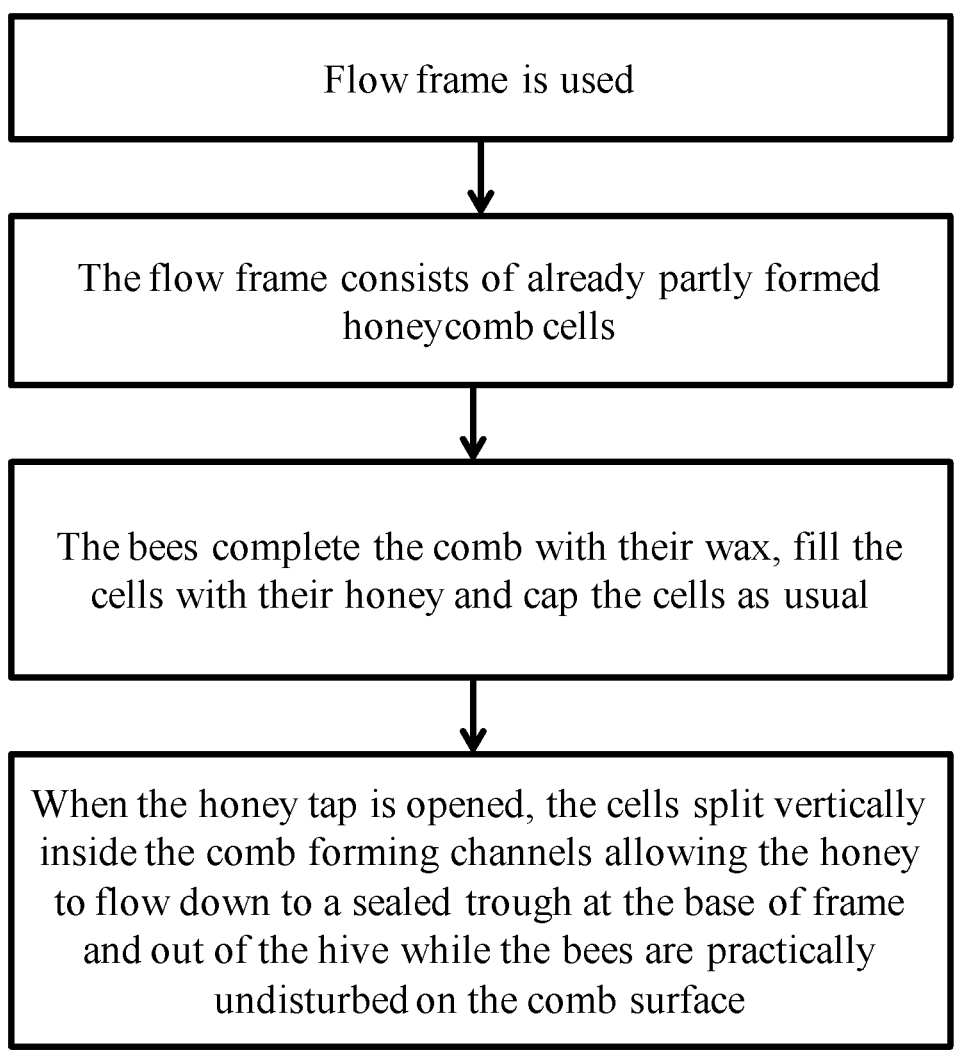
FIG. 2 depicts a flowchart for method of honey tapping.

FIG. 1 depicts a flowchart for method of honey extraction. In another embodiment, extraction of honey maybe performed by honey tapping using flow frame bee hives. FIG. 2 illustrates the method of flow frame technique of honey tapping. The flow frame beehives have partly formed honeycomb cells that are completed by the honeybees to store honey. Once the honeybees complete the comb cells with their wax and fill the cells with honey and cap it, honey can be extracted by opening the tap. Opening the tap will split the comb cells vertically allowing the honey to flow down which may then be collected without disturbing the honeybees.

The honey produced according to the various embodiments herein may further be processed by method generally known in the field. In an embodiment, processing may be performed by techniques such as heating directly or indirectly, straining, filtration, etc. In a preferred embodiment, the raw honey is filtered and then heated under controlled conditions. Controlled conditions may be conditions suitable to purify and prevent honey from granulation. In one embodiment, controlled conditions for processing include controlled temperature of about 61° C. to 63° C., for a maximum period of about 30 minutes and until the humidity is within the range of 18% to 22%. In an embodiment, heating is performed to ensure pasteurization and may be performed by using a power blanket or direct heat.

Figure 3:
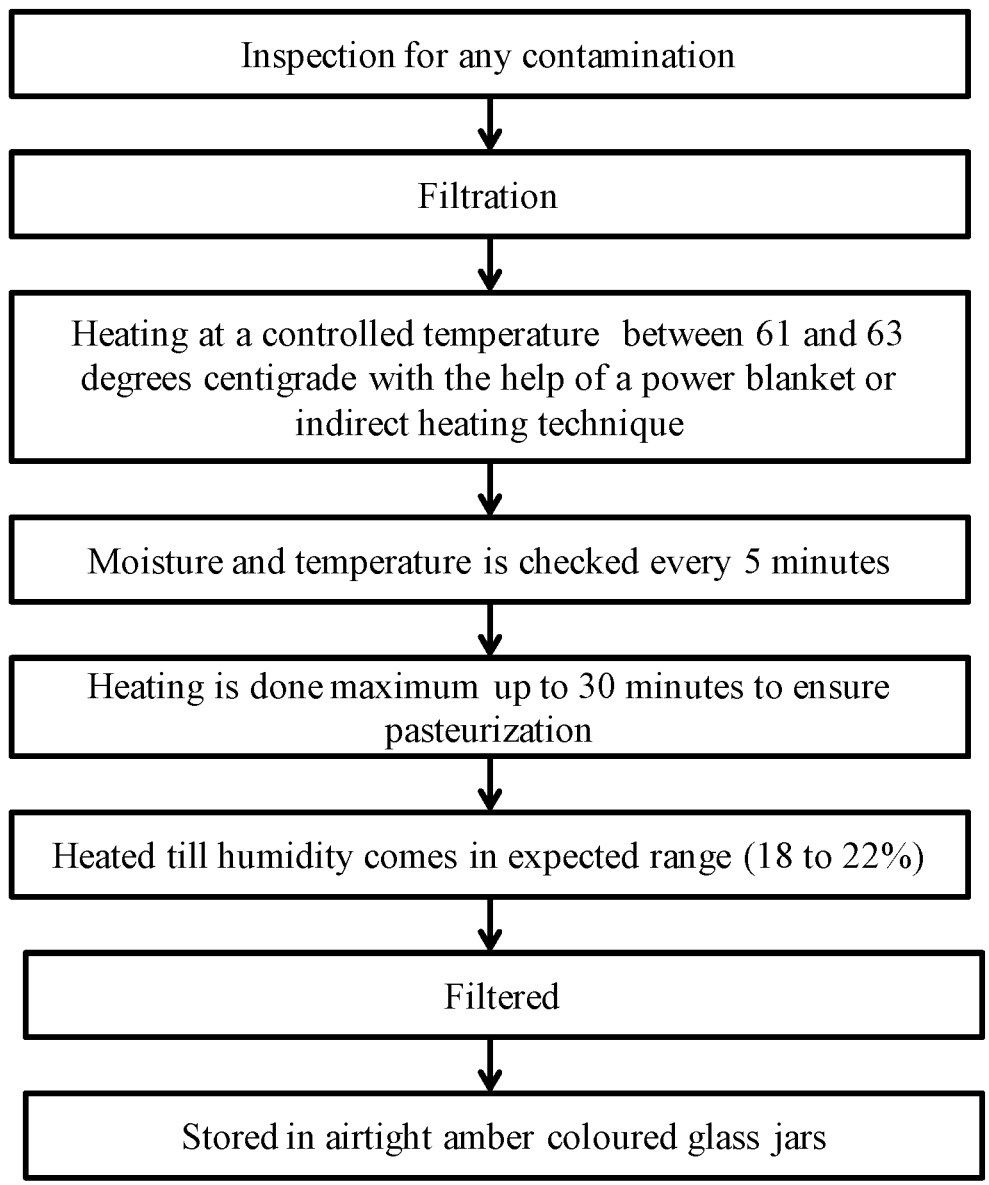
FIG. 3 depicts a flowchart for method of obtaining processed honey from raw honey; according to embodiments as disclosed herein.

In an embodiment, the method of preparation of medicated honey may further include packaging of the processed honey in airtight amber color containers. It would be apparent to a person skilled in the art that many modifications in the method may be practiced without departing from the scope of the present invention. FIG. 3 depicts a flowchart for method of processing medicated honey as disclosed in the various embodiments herein.

Treatment

Disclosed herein are embodiments of a method for the management and prevention of cancer. Also disclosed herein are methods of strengthening the immune system. In an embodiment, the method includes administering to a subject a suitable amount of medicated honey disclosed in the various embodiments herein.

Embodiments of the Disclosed composition may also find use in the preparation of a medicament having antioxidant properties. It may also be used in the preparation of medication for the prevention/management of cancer. Further embodiments of the disclosed composition may also be used as a medium for the administration of medicine. The term medicine may include any ayurvedic or allopathic medicine which may be mixed or triturated to improve its absorption or palatability. It may further include any therapeutic agent known to be administered with honey.

In an embodiment, the honey administered may be raw honey or processed honey. In another embodiment, the honey may be combined with other ingredients such as minerals, vitamins, amino acids, herbal extracts, therapeutic agents, etc. The therapeutic agents that may be used include anti-oxidants, anticancer, antimicrobial, antiulcer, cytoprotective, chemoprotective, wound healing, anti-acne, hepatoprotective, antiviral, filaricidal, anti-allergy, anti-diabetic, analgesic, antipyretic agents and so on.

Subject may include any individual, child or adult. In an embodiment, subject includes an individual having cancer. In another embodiment, subject includes any individual having poor health conditions. In another embodiment, the disclosed honey may be used to improve general health of any individual. Accordingly, the subject may include any individual looking at improving general health.

Embodiments of the Disclosed formulation (also referred as Test substance) was further evaluated for cytotoxicity and anti-oxidant properties by studies, as described hereunder by way of examples. Embodiments are further described by reference to the following examples by way of illustration only and should not be construed to limit the scope of the claims provided herewith. It will be apparent to those skilled in the art that many modifications, both to materials and methods, may be practiced without departing from the scope of the claims.

Example 1: Evaluation of In Vitro Cytotoxicity of Medicated Honey on Selected Cell Lines Objective: The purpose of this Study is to evaluate the test substance (medicated honey) for its cytotoxicity against selected cell lines.

Summary: In-vitro cytotoxicity of the test substance (medicated honey) was tested by MTT on A549 (Human Lung Carcinoma), HeLa (Human Cervix Adenocarcinoma) and HL-60 (Human promyeloblast leukemia) cell lines. The test substance was taken at concentrations ranging from 1000 µg/ml to 7.8 µg/ml (i.e. 1000 µg/ml, 500 µg/ml, 250 µg/ml, 125 µg/ml, 62.5 µg/ml, 31.25 µ/ml, 15.6 µg/ml and 7.8 m/ml) to determine the percentage growth inhibition on the cell lines A549 and HeLa.

Observation: It was observed that the Test substance exhibited a CTC50 value of >1000 on all three cell lines (A549, HeLa and HL-60). Table 2 depicts the Cytotoxicity levels of test substance against A549 cell line. Table 3 depicts the Cytotoxicity levels of test substance against HeLa cell line. Table 4 depicts the Cytotoxicity levels of test substance against HL-60 cell line.

TABLE 2

Cytotoxic properties of test substances against A549 cell line

| No | Name of Test Substance | Test Conc. (µg/ml) | % Cytotoxicity | CTC50 (µg/ml) |
|---|---|---|---|---|
| 1. | Medicated honey | 1000 | 26.05 ± 0.93 | >1000 |
| | | 500 | 18.70 ± 0.93 | |
| | | 250 | 14.24 ± 0.51 | |
| | | 125 | 12.94 ± 0.64 | |
| | | 62.5 | 10.96 ± 0.68 | |
| | | 31.25 | 6.84 ± 1.37 | |
| | | 15.6 | 2.99 ± 0.43 | |
| | | 7.8 | 1.53 ± 0.34 | |

TABLE 3

Cytotoxic properties of test substances against HeLacell line

| No | Name of Test Substance | Test Conc. (µg/ml) | % Cytotoxicity | CTC50 (µg/ml) |
|---|---|---|---|---|
| 1. | Medicated honey | 1000 | 24.97 ± 1.02 | >1000 |
| | | 500 | 18.70 ± 0.93 | |
| | | 250 | 14.24 ± 0.51 | |
| | | 125 | 12.94 ± 0.64 | |
| | | 62.5 | 10.96 ± 0.68 | |

TABLE 3-continued

Cytotoxic properties of test substances against HeLacell line

| No | Name of Test Substance | Test Conc. (μg/ml) | % Cytotoxicity | CTC50 (μg/ml) |
|---|---|---|---|---|
| | | 31.25 | 6.84 ± 1.37 | |
| | | 15.6 | 2.99 ± 0.43 | |
| | | 7.8 | 1.53 ± 0.34 | |

TABLE 4

Cytotoxic properties of test substances against HL-60cell line

| No | Name of Test Substance | Test Conc. (μg/ml) | % Cytotoxicity | CTC50 (μg/ml) |
|---|---|---|---|---|
| 1. | Medicated honey | 1000 | 41.43 ± 0.56 | >1000 |
| | | 500 | 37.03 ± 0.56 | |
| | | 250 | 32.83 ± 0.30 | |
| | | 125 | 30.86 ± 0.41 | |
| | | 62.5 | 29.88 ± 1.33 | |
| | | 31.25 | 16.70 ± 0.51 | |
| | | 15.6 | 7.76 ± 0.38 | |
| | | 7.8 | 3.76 ± 0.47 | |

Example 2: Evaluation of Antioxidant Activity of Medicated Honey

Objective: To assess the antioxidant activity of medicated honey by ABTS, Nitricoxide, Hydroxyl radical and Reducing power assay method.

Summary: The antioxidant activity for ABTS at 2000 to 125 μg/ml (i.e. 2000 μg/ml, 1000 μg/ml, 500 μg/ml, 250 μg/ml and 125 μg/ml), Nitric oxide at 5000 to 312.5 μm/ml (i.e. 5000 μg/ml, 2500 μg/ml, 1250 μg/ml, 625 μg/ml, 312.5 μg/ml), Hydroxyl radical and Ferric ion reducing power assay both at 1000 to 62.5 μg/ml (1000 μg/ml, 500 μg/ml, 250 μg/ml, 125 μg/ml and 62.5 μg/ml) were performed.

Observation: The antioxidant activity of the test samples exhibited the IC50 value of greater than 1000. The reducing power assay revealed the RPA value ranging from 0.082 to 0.024 for Medicated honey. Table 5 depicts the antioxidant activity of test substance for ABTS radical. Table 6 depicts the antioxidant activity of test substance for Nitric oxide radical. Table 7 depicts the antioxidant activity of test substance for Hydroxyl radical. Table 8 depicts the antioxidant activity of test substance for Hydroxyl radical.

TABLE 5

The antioxidant activity of test substance for ABTS radical

| No | Test Substance | Concentration (μg/ml) | % Inhibition | IC50 (μg/ml) |
|---|---|---|---|---|
| 1. | Medicated honey | 2000 | 61.83 + 0.95 | 1528.788 ± 1.05 |
| | | 1000 | 36.47 + 3.66 | |
| | | 500 | 33.28 + 2.65 | |
| | | 250 | 17.64 + 1.57 | |
| | | 125 | 12.01 + 1.79 | |

TABLE 6

The antioxidant activity of test substance for Nitric oxide radical

| No | Test Substance | Concentration (μg/ml) | % Inhibition | IC50 (μg/ml) |
|---|---|---|---|---|
| 1. | Medicated honey | 5000 | 33.53 + 1.87 | >5000 |
| | | 2500 | 19.08 + 4.50 | |
| | | 1250 | 16.01 + 3.54 | |
| | | 625 | — | |
| | | 312.5 | 9.53 + 3.56 | |

TABLE 7

The antioxidant activity of test substance for Hydroxyl radical

| No | Test Substance | Concentration (μg/ml) | % Inhibition | IC50 (μg/ml) |
|---|---|---|---|---|
| 1. | Medicated honey | 1000 | 8.09 ± 0.91 | >5000 |
| | | 500 | 6.73 ± 0.36 | |
| | | 250 | 0.48 ± 0.72 | |
| | | 125 | — | |
| | | 62.5 | — | |

TABLE 8

The antioxidant activity of test substance for Hydroxyl radical

| No | Test Substance | Concentration (μg/ml) | RPA |
|---|---|---|---|
| 1. | Medicated honey | 1000 | 0.082 |
| | | 500 | 0.053 |
| | | 250 | 0.050 |
| | | 125 | 0.039 |
| | | 62.5 | 0.024 |

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein.

I claim:

1. A medicated honey produced by a method comprising:
providing honeybees with a bee-feed comprising *Plumeria rubra, Vinca rosea, Ageratum conyzoides, Calotropis gigantea, Calotropis procera, Nerium indicum, Thevetia neriifolia, Jasminum officinale, Jasminum auriculatum, Musa paradisiaca, Jasminum humile, Nyctanthes abor-tristis, Ocimum sanctum, Ocimum gratissimum, Tabernaemontana divaricata, Tridax procumbens, Cassia auriculata, Hibiscus vitifolius, Sesbania grandiflora, Nymphaea alba, Saraca asoca, Hibiscus alba, Couroupita guianensis* and *Plumbago rose*, in a controlled system maintained at a temperature in the range of 32° C. to 36° C. and relative humidity in the range of 60% to 75%;
extracting honey produced by the honeybees; and processing the extracted honey by heating the honey at a temperature in the range of 61° C. to 63° C. while maintaining humidity in the range of 18% to 22%, wherein said honey exhibits antioxidant activity.

2. The medicated honey as claimed in claim 1, wherein said bee-feed comprises of nectar obtained from at least one plant selected from a group consisting of *Plumeria rubra, Vinca rosea, Ageratum conyzoides, Calotropis gigantea, Calotropis procera, Nerium indicum, Thevetia neriifolia, Jasminum officinale, Jasminum auriculatum, Musa paradisiaca, Jasminum humile, Nyctanthes abor-tristis, Ocimum sanctum, Ocimum gratissimum, Tabernaemontana divaricata, Tridax procumbens, Cassia auriculata, Hibiscus vitifolius, Sesbania grandiflora, Nymphaea alba, Saraca asoca, Hibiscus alba, Couroupita guianensis* and *Plumbago rosea*.

3. The medicated honey as claimed in claim 1, wherein bee-feed is made available to the honeybees for a period of 100 to 150 days.

4. The medicated honey as claimed in claim 1, wherein said method further includes packaging in airtight amber color containers.

5. The medicated honey as claimed in claim 1, wherein said medicated honey exhibits a reducing power assay (RPA) value in the range of 0.082 to 0.024.

6. A method of producing medicated honey, comprising of:
providing bees with a bee feed comprising *Plumeria rubra, Vinca rosea, Ageratum conyzoides, Calotropis gigantea, Calotropis procera, Nerium indicum, Thevetia neriifolia, Jasminum officinale, Jasminum auriculatum, Musa paradisiaca, Jasminum humile, Nyctanthes abor-tristis, Ocimum sanctum, Ocimum gratissimum, Tabernaemontana divaricata, Tridax procumbens, Cassia auriculata, Hibiscus vitifolius, Sesbania grandiflora, Nymphaea alba, Saraca asoca, Hibiscus alba, Couroupita guianensis* and *Plumbago rosea* in a controlled system maintained at a temperature in the range of 32° C. to 36° C. and relative humidity in the range of 60% to 75%; extracting honey produced by the honeybees; and processing the extracted honey by heating the honey at a temperature in the range of 61° C. to 63° C. while maintaining humidity in the range of 18% to 22%, wherein said honey exhibits antioxidant activity.

7. The method of producing medicated honey as claimed in claim 6, wherein said bee-feed is made available to honeybees for a period of 100 to 150 days.

8. The method of producing medicated honey as claimed in claim 6, wherein heating is performed for a period of 10 to 30 minutes.

9. The method as claimed in claim 6, wherein said medicated honey exhibits a reducing power assay (RPA) value in the range of 0.082 to 0.024.

10. A method for strengthening the immune system, comprising administering a therapeutically effective amount of medicated honey claimed in claim 1.

* * * * *